United States Patent
Horn et al.

(10) Patent No.: US 9,090,523 B1
(45) Date of Patent: Jul. 28, 2015

(54) PROCESS FOR FLUSHING TOP AND BOTTOM HEADS OF A VESSEL

(71) Applicant: UOP LLC, Des Plaines, IL (US)

(72) Inventors: Ian G. Horn, Streamwood, IL (US); Jason T. Corradi, Arlington Heights, IL (US); Gregory R. Werba, Arlington Heights, IL (US); Partick Whitchurch, Sleepy Hollow, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/194,994

(22) Filed: Mar. 3, 2014

(51) Int. Cl.
*C07C 7/12* (2006.01)
*C07C 7/09* (2006.01)
*C07C 7/00* (2006.01)

(52) U.S. Cl.
CPC . *C07C 7/12* (2013.01); *C07C 7/005* (2013.01); *C07C 7/09* (2013.01)

(58) Field of Classification Search
None
See application file for complete search history.

(56) References Cited

U.S. PATENT DOCUMENTS

| | | | |
|---|---|---|---|
| 4,961,881 A * | 10/1990 | Ou | 554/193 |
| 5,595,665 A * | 1/1997 | Noe | 210/662 |
| 7,011,759 B1 | 3/2006 | Corradi | |
| 7,473,368 B2 | 1/2009 | Hotier | |
| 7,635,795 B2 | 12/2009 | Lee et al. | |
| 7,915,471 B2 | 3/2011 | Leflaive et al. | |
| 8,013,202 B2 | 9/2011 | Lee et al. | |
| 8,211,312 B2 | 7/2012 | Stewart et al. | |
| 8,580,120 B2 | 11/2013 | Porter | |
| 2011/0282125 A1 * | 11/2011 | Noe et al. | 585/822 |
| 2012/0302812 A1 * | 11/2012 | Corradi et al. | 585/821 |
| 2013/0158333 A1 | 6/2013 | Corradi | |
| 2013/0158334 A1 | 6/2013 | Corradi | |
| 2013/0317261 A1 * | 11/2013 | Sharma et al. | 568/917 |
| 2014/0288345 A1 * | 9/2014 | Corradi | 585/828 |

FOREIGN PATENT DOCUMENTS

CN  101734989 B  10/2013

* cited by examiner

*Primary Examiner* — Tam M Nguyen

(57) ABSTRACT

A process for flushing the rounded top head and rounded bottom head of a vessel used in an adsorption process in which the rounded top head and the rounded bottom head of the vessel are flushed with a flush fluid. The extract stream from the adsorption process is split into a desorbent rich stream and desorbent lean steam. The flushing fluid is a fraction separated from a desorbent lean split of the extract stream.

17 Claims, 3 Drawing Sheets

PROCESS FOR FLUSHING TOP AND BOTTOM HEADS OF A VESSEL

FIELD OF THE INVENTION

This invention relates generally to the processing of fluids over particulate solids. More specifically, this invention relates to the fluid used to flush the tops and bottoms of vessels containing particulate solids.

BACKGROUND OF THE INVENTION

Petroleum refining and petrochemical processes frequently involve the processing of fluids over particulate solids contained within a pressure vessel. Internal partitions can subdivide the interior of a pressure vessel into different chambers to permit staged or multiple contacting operations within a single vessel. These partitions routinely take the form of, or are used in conjunction with, collection or distribution grids. Process requirements, such as the collection and distribution of fluids, regularly dictate the employment of flat partitions. Concomitantly, pressure vessels usually are closed by rounded "heads" at each end. The rounded head and flat interior partitions at each end of a vessel create a head space whose configuration is not suited to process purposes, risking contamination or deterioration of the process if this head space itself becomes contaminated and subsequently mixes with the high purity process fluid.

Further, flat partitions are subject to structural damage from differential pressures of as little as 15 kPa or even less across the partition. Structural damage to a partition has the potential to create leaks across the partition or in associated distribution/collection piping.

Thus, maintaining structural integrity of interior end partitions requires pressure balancing between the head space and the adjoining volume on the process side of the partition. The head space can serve as an equalization chamber through a small opening or port in the partition communicating head fluid to and from the process chamber on the opposite side of the partition. However, this arrangement risks some inefficiency in the process through process fluid passing into the head space, resulting in some loss in yield. Alternatively, subsequent reversal of flow of the head fluid into the process chamber has the potential to contaminate the process and final product.

A specific technology which illustrates the above problem is the simulated moving bed ("SMB") adsorbent process described in U.S. Pat. No. 2,985,589. The process distributes and collects process streams from multiple chambers with multiple zones, or beds, of adsorbent defined by internal partitions located within a pressure vessel and arranged as distribution/collection grids. Periodic shifting of the input and effluent streams through the chambers simulates movement of the adsorbent and permits delivery or withdrawal of process streams with a desired concentration via flat distribution grids.

The head space resulting from the flat distribution grids and a concave end is flushed by a small flow of a flush fluid, usually comprising a desorbent material. A desorbent material normally is selected so that passage of this material into the adsorbent bed through a grid opening does not contaminate the products of the process.

However, the periodic shifting of the input and effluent streams through the chambers of adsorbent can effect a buildup of contaminants in the desorbent through leakage through the grid opening, particularly in the bottom head of the chamber.

Further, the addition of desorbent to the adsorbent bed through the grid opening can interfere with the optimization of purity and recovery by taking up adsorbent capacity and hindering an accurate accounting of flow through the adsorbent beds.

U.S. Pat. No. 5,595,665, incorporated herein by reference in its entirety, addresses some of these issues by channeling the fluid generated by a head flush into a low volume chamber (referred to herein as "snorkel") in the head space and withdrawing fluid from the pressure vessel through the snorkel. Withdrawing fluid generated by the head flush and channeling the fluid through the snorkel reduces or eliminates the circulation of fluid between the equalization chamber and the adjacent process chamber and minimizes the amount of contamination that can result from any circulation of fluid resulting from pressure fluctuations. The withdrawal of fluid through the snorkel also provides a non-contaminating path for withdrawing leakage from the equalization chamber of the vessel.

However, this feature fails to address the fluid that is used as the flush fluid in the system. More specifically, the use of desorbent as a flush fluid unnecessarily increases the energy requirements of the process as the desorbent withdrawn fluid must be recovered and purified via fractionation before re-use in the process.

Therefore, there remains a need for an effective and efficient process for flushing of the various components of a simulated moving bed process.

SUMMARY OF THE INVENTION

A first embodiment of the invention may be characterized as a method for the recovery of a product from a feed stream in which: a feed stream is passed into a simulated moving bed adsorption zone having at least one vessel having a rounded top head and a rounded bottom head; an extract stream from the simulated moving bed adsorption zone is separated in a first fractionation zone into an overhead stream and a bottoms stream, the overhead stream being rich in desorbent, the bottoms stream including the product and additional compounds; the bottom streams from the first fractionation zone is separated in a second fractionation zone into a second overhead stream and a second bottoms stream, the second overhead stream being rich in product, the second bottom stream comprising the additional compounds; and, the rounded top head of the at least one vessel and the rounded bottom head of the at least one vessel are flushed with a portion of the second bottoms stream from the second fractionation zone to provide a flush fluid.

A second embodiment of the invention may be characterized as a process for the recovery of a product from a feed stream in which: a feed stream is passed into a simulated moving bed adsorption zone having at least one vessel having a rounded top head and a rounded bottom head; an extract stream from the simulated moving bed adsorption zone is separated in a first fractionation zone into a desorbent rich stream and a desorbent lean stream; the desorbent lean stream is separated into a product rich stream and a flush fluid stream; and, the rounded top head of the at least one vessel and the rounded bottom head of the at least one vessel are flushed with at least a portion of the flush fluid.

Another embodiment of the invention may be characterized as a method for the recovery of paraxylene from a feed stream in which: a feed stream is passed through a valve into an adsorption zone having at least one vessel in which paraxylene is adsorbed, the at least one vessel having a rounded top head and a rounded bottom head; a raffinate is withdrawn from the adsorption zone through the valve; a desorbent is passed through a valve into the at least one vessel to desorb the paraxylene in an extract stream; the extract stream is withdrawn from the adsorption zone through the valve; the extract stream is passed from the valve to a first fractionation zone in which the extract stream is separated into a bottoms stream and an overhead stream, wherein the overhead stream comprises a desorbent rich stream and the bottoms stream comprises paraxylene and heavy compounds; the bottoms stream of the first fractionation zone is passed to a second fractionation zone in which the bottoms stream of the first fractionation zone is separated into a second overhead stream and a second bottoms stream, the second overhead stream comprising a paraxylene rich stream and the second bottoms stream comprising the heavy compounds; a portion of the second bottoms stream is recovered as a flush fluid; the top head of the at least one vessel is flushed with the flush fluid; the bottom head of the at least one vessel is flushed with the flush fluid; and, the valve is flushed with the flush fluid.

Additional objects, embodiments, and details of the invention are set forth in the following detailed description of the invention.

DETAILED DESCRIPTION OF THE DRAWINGS

The drawings are simplified process diagrams in which.

DETAILED DESCRIPTION OF THE INVENTION

A method has been developed in which a portion of a fraction separated from a desorbent lean stream split of an extract stream is used to flush the heads of the adsorption chamber which was used to produce the extract stream.

Figure 1:
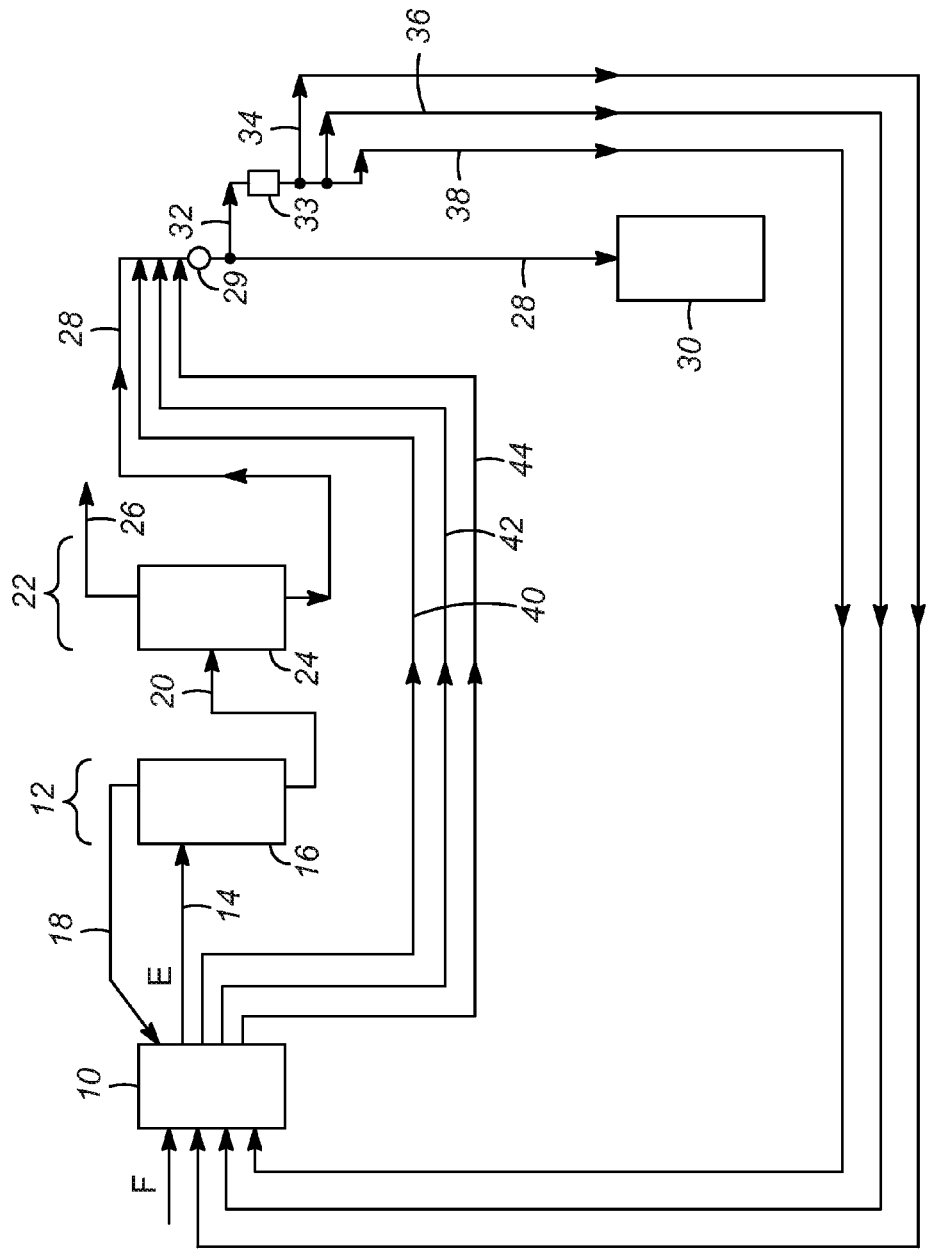
FIG. 1 shows a process flow diagram of a process using flush fluid for an adsorption zone according to one or more embodiments of the present invention.

As shown in FIG. 1, a feed stream F is passed into an adsorption zone 10 and an extract stream E is recovered from the adsorption zone 10.

Figure 2:
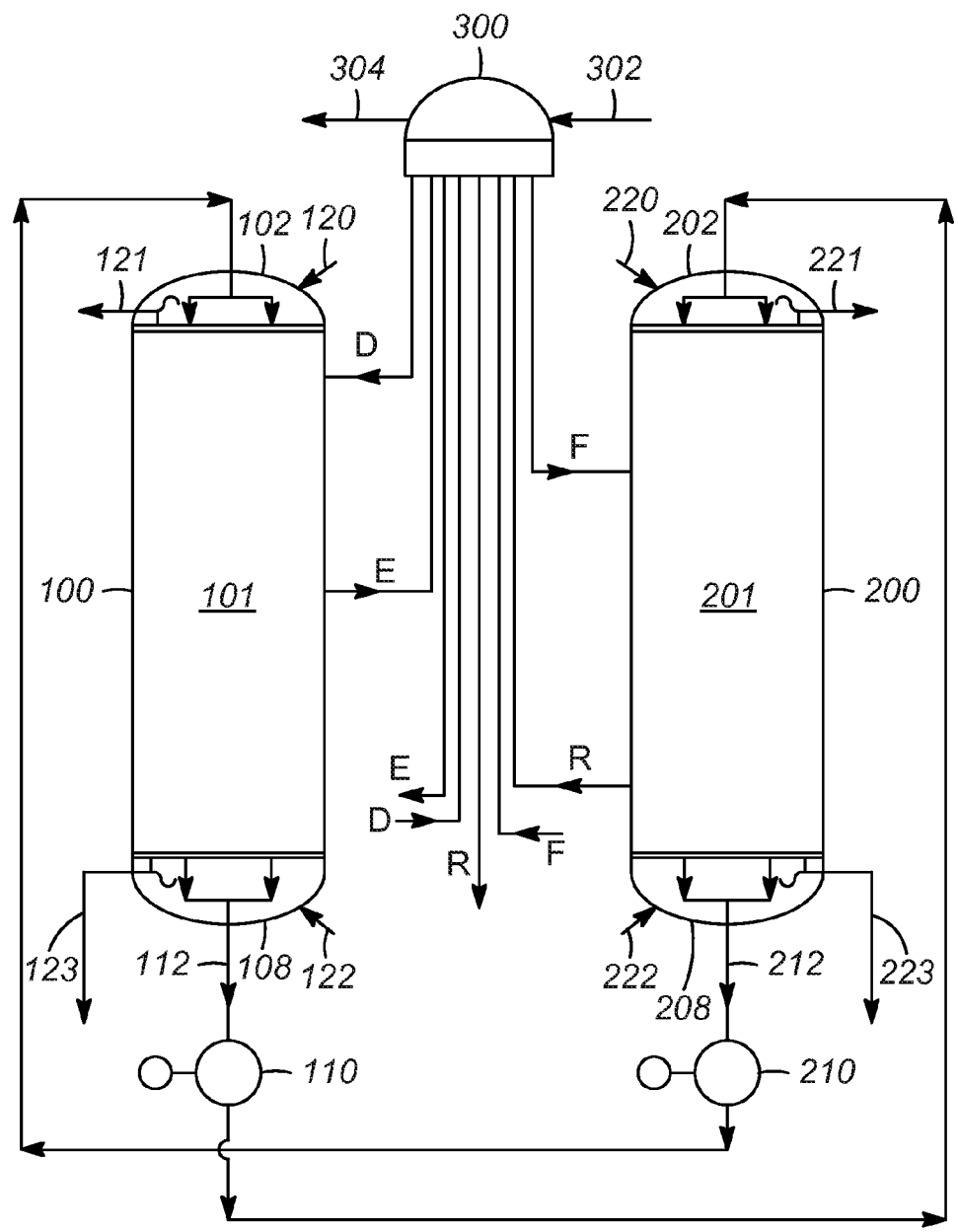
FIG. 2 shows a diagram of a simulated moving bed adsorption process utilized in connection with the flush fluid according to one or more embodiments of the present invention.
Figure 3:
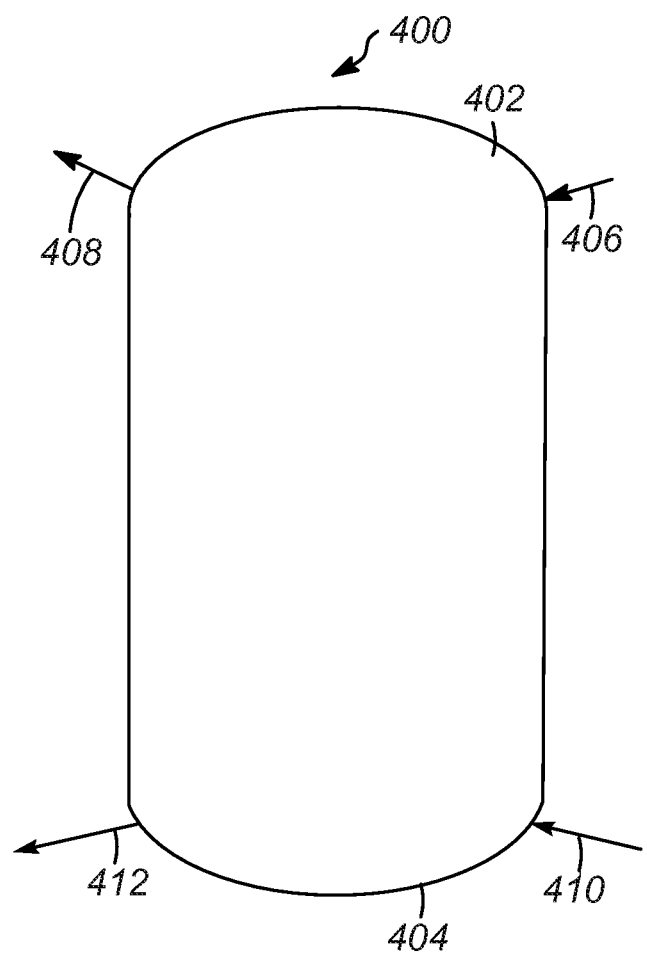
FIG. 3 shows a diagram of a single vessel adsorption process utilized in connection with the flush fluid according to one or more embodiments of the present invention.

The adsorption zone 10 can be a simulated moving bed adsorption zone having two vessels and a valve (see, FIG. 2), or merely an adsorption zone having one vessel (see, FIG. 3). The different simulated adsorption zones shown in FIGS. 2 and 3 are discussed in more detail below.

Returning to FIG. 1, the extract stream E is passed to a first fractionation zone 12 and preferably, the extract stream E passes via a line 14 into a first separator 16. Within the first separator 16 of the first fractionation zone 12, the extract stream E is separated into an overhead stream and a bottoms stream. In the preferred embodiment the first separator 16 is an extract column which is a fractional distillation column having trays, packing, or both, as known in the art.

The top stream from the first separator 16 comprises desorbent, and thus is a desorbent rich stream. The bottoms stream from the first separator 16 comprises the desired product and additional compounds and thus is a desorbent lean stream. As will be appreciated by those of ordinary skill in the art, when separating hydrocarbons, there typically is some crossover between the various fractions/streams during the separation processes and thus, the present invention is intended to accommodate the crossover amounts of compounds. Moreover, as will be appreciated, the amount of crossover may be adjusted based upon economic conditions and optimization of equipment cost and energy use.

The overhead stream may be recovered via a line 18 and returned to the adsorption zone 10 via line 18 as desorbent for the adsorption process. In certain embodiments, the desorbent is selected from the group consisting of para-diethylbenzene, para-diisopropylbenzene, tetralin, and the like, and combinations thereof. In certain embodiments, toluene and the like can also be used as the desorbent. The para-diethylbenzene has a higher boiling point than the $C_8$ aromatic isomers and, as such, the para-diethylbenzene will be a bottoms (i.e., heavy) product when separated from the $C_8$ isomers in a fractional distillation column. Similarly, toluene has a lower boiling point than the $C_8$ aromatic isomers and, as such, the toluene is the overhead (i.e., light) product when separated from the $C_8$ isomers in a fractional distillation column.

As shown in FIG. 1, the bottom stream is passed from the first fractionation zone 12 via a line 20 to a second fractionation zone 22 including a second separator 24, preferably a column. In the preferred embodiment in which the desired product is paraxylene, the second column preferably comprises a paraxylene column which is also a fractional distillation column having trays, packing, or both, as known in the art.

In the second separator 24, the bottoms stream from the first fractionation zone 12 is separated into an overhead stream and a bottoms stream. The overhead stream from the second separator 24 comprises a stream rich in product and can be recovered via a line 26. The further processing and treatment or storage of this stream is not necessary for understanding and practicing the present invention.

Returning to the second separator 24, the bottoms stream from the second separator 24 may also contain some of the desired product. It is contemplated that for energy conservation reasons, the amount of product in the bottoms stream is higher than typical tolerances.

The bottoms stream may be sent via a line 28 with a pump 29 to a further processing zone 30, which may comprise further fractional distillation, reaction operations, or both. For example, the bottom stream may be sent to an A8 Rerun Column and returned back to the adsorption zone 10 to recover the product from the stream (not shown). Again, the further processing zone 30 and the treatment or storage of this stream is not necessary for understanding and practicing the present invention.

Rather, as shown in FIG. 1, in the present invention, a side draw line 32 off of the line 28 is used to recover a portion of the bottoms stream of the second separator 24 of the second fractionation zone 22.

From here, the recovered portion may be cooled in a cooler 33 and sent as flush fluid via lines 34, 36, 38 to flush to the adsorption zone 10. The cooler 33 is used to lower a temperature of the recovered portion to a temperature that is approximately the same as the temperature of the fluids in the adsorption zone 10. As will be appreciated, the cooler may be an air cooler, a water cooler, a process stream cooler, or a combination of these.

As shown in FIG. 2, the adsorption zone 10 in one embodiment comprises a simulated moving bed adsorption process used in association with the present invention sequentially contacts a feed stream "F" with adsorbent contained in the vessels and a desorbent "D" to recover an extract stream "E" and a raffinate stream "R". Countercurrent moving bed or simulated moving bed countercurrent flow systems have a much greater separation efficiency than fixed-bed systems, as adsorption and desorption operations are continuously taking place with a continuous feed stream and continuous production of extract and raffinate. In the simulated moving bed countercurrent flow system, progressive shifting of multiple liquid feed and product access points down an adsorbent chamber simulate the upward movement of adsorbent contained in the chamber.

The various streams involved in simulated moving bed adsorption as illustrated in FIG. 2 may be characterized as follows. A "feed stream" is a mixture containing one or more extract components and one or more raffinate components to be separated by the process. The "extract stream" comprises a component, usually the desired product, which is more selectively adsorbed by the adsorbent. The "raffinate stream" comprises components which are less selectively adsorbed. "Desorbent" refers to a material capable of desorbing an extract component, which generally is inert to the components of the feed stream and easily separable from the extract and raffinate. The extract stream E and raffinate stream R from the illustrated scheme generally contain desorbent, which usually is separated from extract and raffinate components by conventional fractionation, discussed above, and returned to the process in stream D.

The adsorbent in a simulated moving bed adsorption process is contained in multiple beds in one or more vessels; two vessels 100, 200 in series are shown in FIG. 2. Each vessel contains multiple beds of adsorbent in processing spaces 101, 201, respectively. Each of the vessels has a number of access points relating to the number of beds of adsorbent, and the position of the feed stream F, desorbent input D, extract stream E and raffinate stream R are shifted along the access points to simulate a moving adsorbent bed. A valve 300 effects the shifting of the streams to simulate countercurrent flow and withdraws and supplies the fluids to each vessels 100, 200. A preferred valve 300 is a rotary disc type valve as characterized for example in U.S. Pat. Nos. 3,040,777 and 3,422,848. Additionally, it is contemplated that the valve comprises one or more valves instead of a single valve. In other words, one valve can be used to introduce fluids, another can be used to remove fluids, and another can be used to circulate fluids.

Circulating liquid comprising desorbent, extract and raffinate circulates through the each vessel 100, 200 through pumps 110, 210, respectively. Systems to control the flow of circulating liquid are described in U.S. Pat. No. 5,595,665, but the particulars of such systems are not essential to the present invention.

The active liquid access points effectively divide the adsorbent chamber into separate zones which move as the access points are shifted. The adsorption zone is located between the feed inlet stream F and the raffinate outlet stream R. In this zone, the feedstock contacts the adsorbent, an extract component is adsorbed, and a raffinate stream is withdrawn. Immediately upstream with respect to fluid flow is the purification zone, defined as the adsorbent between the extract outlet stream E and the feed inlet stream F. In the purification zone, the raffinate component is displaced from the nonselective void volume of the adsorbent and desorbed from the pore volume or surface of adsorbent shifting into this zone by passing a portion of extract stream material leaving the desorption zone. The desorption zone, upstream of the purification zone, is defined as the adsorbent between the desorbent inlet D and the extract stream outlet E. The desorbent passing into this zone displaces the extract component which was adsorbed by previous contact with feed in the adsorption zone. A buffer zone between the raffinate outlet stream R and the desorbent inlet stream D conserves the amount of desorbent utilized in the desorption step, in that a portion of the raffinate stream enters the buffer zone to displace desorbent material present in that zone into the desorption zone. The buffer zone contains enough adsorbent to prevent raffinate from passing into the desorption zone and contaminating the extract stream.

Usually the adsorbent chamber is divided into multiple compartments or "beds" as described in U.S. Pat. No. 2,985,589. The positions of the various streams described above are shifted along a series of access points relating to the number of beds. This arrangement eases the distribution of fluids into and out of the chamber through eliminating channeling and other inefficiencies, prevents convective back-mixing of fluid in a direction opposite to that of primary fluid flow, and prevents migration of adsorbent through the chamber. The beds are separated by profile wire screens covering the cross section of the vessel.

In other designs, the wire screens are eliminated and a united adsorbent mass is supported on the lower distribution grid in each chamber. As the access points are into the adsorbent mass rather than between adsorbent beds, feed and product distributors must be designed to minimize the impact of flows on the adsorbent. To avoid plugging of the adsorbent mass with any debris entering with the feed or desorbent and to eliminate the loss of adsorbent fines leaving with the extract and raffinate in this embodiment, in-line strainers are installed on each of the access points. Effective strainers are well known in the industry, and the strainers may be of any design suitable for the separation of solids from hydrocarbon streams. Since each of the access points at different times will enable feed or desorbent to enter the chamber and products to leave the chamber, the strainers should be in a bi-directional arrangement; that is, two profile wire screens should be oriented at each of the access points such that the flat face of one screen always is exposed to the oncoming flow. The bi-directional flow of feed and product provides repeated back flushing of each screen in the strainer, flushing outside debris away from the chamber and adsorbent particles back into the chamber.

As shown in FIG. 2, the two vessels 100, 200 each include rounded top heads 102, 202. The feed stream F is introduced into the simulated moving bed adsorption process via the valve 300. Circulating fluid enters each vessel 100, 200. The circulating fluid leaves the respective vessels, after passing through a rounded bottom head 108, 208. Then, through lines 112, 212, and is passed through pumps 110, 210 to the other vessel in series, i.e., through the first pump 110 to the second vessel 200 and through the second pump 210 to the first vessel 100.

The flush fluid from one of the flush fluid lines 34, 36, 38 (see, FIG. 1) may be passed into the top heads 102, 202 of the vessels 100, 200 through lines 120, 220. A recovered flush fluid may be removed from the top heads 102, 202 of the vessels 100, 200 via lines 121 and 221.

In the lower part of each vessel 100, 200, flush fluid from one of the flush fluid lines 34, 36, 38 (see, FIG. 1) may be passed into the rounded bottom heads 108, 208 of the vessels 100, 200 through lines 122, 222. A recovered flush fluid may be removed from the rounded bottom heads 108, 208 of the vessels 100, 200 via lines 123 and 223.

Furthermore, the valve 300 may also have flush fluid from one of the flush fluid lines 34, 36, 38 (see, FIG. 1) introduced via a line 302 and removed via a line 304.

The amount of fluid circulated through the head is independent of the process fluid circulated through the system. If the head flush contains a negligible level of valuable contaminants, as is usually the case in the top equalization space and snorkel of a chamber, the flow typically is set at a rate that will displace the volume of the flush chamber once in every step of the multi-step cycle. If the head flush contains valuable components to be recovered according to the present invention, the flow rate is less than 10 volume %, and generally below 1%, of the circulating fluid; usually the flow rate is around 0.1% or less of the circulating fluid.

As shown in FIG. 3, another simulated moving bed adsorption process used in the association with the present invention may simply comprise a single vessel 400 having a rounded top head 402 and a rounded bottom head 404. Flush fluid from one of the flush fluid lines 34, 36, 38 (see, FIG. 1) may be passed into the rounded top head 402 via a line 406 and withdrawn via a line 408. Similarly, flush fluid from one of the flush fluid lines 34, 36, 38 (see, FIG. 1) may be passed into the rounded bottom head 404 via a line 410 and withdrawn via a line 412.

Returning to FIG. 1, the flush fluid used to flush the top and bottom heads of the vessel(s) or the valve may be recovered from the adsorption zone 10 via lines 40, 42, 44.

As will be appreciated by one of ordinary skill in the art, the flush fluid recovery lines 121, 221, 123, 223, 304 in the system shown in FIG. 2 and the flush fluid recovery lines 408, 412 shown in FIG. 3 and the flush fluid recovery lines 40, 42, 44 shown in FIG. 1 are merely exemplary of the present invention. One of ordinary skill in the art will appreciate that the numbering of same is not needed to understand or practice the present invention.

Similarly, the number of flush fluid lines 34, 36, 38 taken via the side draw line 32 in FIG. 1, the number of flush fluid delivery lines 120, 122, 220, 222, 302 shown in FIG. 2, and the number of flush fluid delivery lines 406, 410 shown in FIG. 3 are likewise intended only to be exemplary of the present invention.

Returning to FIG. 1, the recovered flush fluid in the flush fluid recovery lines 40, 42, 44 can be passed to the line 28 out of the second separator 24. It is preferred that the flush fluid is then passed again to the side draw line 32 and through one of the flush fluid lines 34, 36, 38 so that the flush fluid will recycle in a recycle loop as recycled flush fluid.

In a preferred embodiment, the flush fluid that is recovered from the bottom head(s) of the vessel(s) will be passed via line 28 to the further processing zone 30 with the remaining portion of the bottom stream from the second fractionation zone 22. At the same time, the other flush fluid will continue to be circulated as recycled flush fluid.

Since, unlike the conventional processes, the flush fluid according to the present invention is a fraction of the extract stream that is desorbent lean, there may be times when it is necessary to initially or occasionally flush the heads of the vessels or valve with a desorbent. For example, when the process is initially started up, until the flow level of extract stream reaches a predetermined level, desorbent may be used as a flush fluid. Once the predetermined level has been reached, the process may switch from the desorbent to a flush fluid according to one or more embodiments of the present invention.

Accordingly, although not shown in the Figures, the process may include additional valves and lines, which allow for the flush fluid to be switched from the fraction of the extract stream that is desorbent lean to a desorbent stream.

It is also contemplated to use desorbent as a flush fluid if at least one of the recycled flush fluid or the flush fluid exhibits a contamination or other defect that requires it to be purged from the system. However, once the contamination defect is purged from the system, the process may switch back to using a flush fluid according to one or more embodiments of the present invention.

It is believed that one or more of the embodiments of the present invention described herein are beneficial and desirable for a number of reasons. For example, since desorbent is not being used as a flush fluid, the energy consumption of the process will be lower. More specifically, the flush fluid used in the present invention is a normal product typically separated or recovered in the various fractionation stages of the separation processes. Therefore, no additional energy will be necessary to separate out the flush fluid.

Based upon a theoretical modeling of a process producing approximately 1,000,000 metric tonnes of paraxylene per year according to one or more embodiments of the present invention, such a process should save approximately $1.4 million as a result of the lower energy consumption.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for the recovery of a paraxylene from a feed stream comprising:
   passing a feed stream into a simulated moving bed adsorption zone having at least one vessel having a rounded top head and a rounded bottom head;
   separating an extract stream from the simulated moving bed adsorption zone in a first fractionation zone into a overhead stream rich in desorbent and a bottoms stream comprising paraxylene and additional compounds;
   separating the bottoms stream from the first fractionation zone in a second fractionation zone into a second overhead stream rich in paraxylene and a second bottoms stream comprising the additional compounds; and,
   flushing the rounded top head of the at least one vessel and the rounded bottom head of the at least one vessel with a portion of the second bottoms stream from the second fractionation zone to provide a flush fluid.

2. The method of claim 1 further comprising:
   recovering the flush fluid as a recovered flush fluid from at least one of the rounded top head of the at least one vessel or the rounded bottom head of the at least one vessel; and,
   recycling the recovered flush fluid back to at least one of the rounded top head of the at least one vessel or the rounded bottom head of the at least one vessel.

3. The method of claim 2 further comprising:
   passing the recovered flush fluid from the rounded bottom head of the at least one vessel to a processing zone; and,
   recycling the recovered flush fluid from the rounded top head of the at least one vessel back to at least one of the rounded top head of the at least one vessel or the rounded bottom head of the at least one vessel.

4. The method of claim 1 further comprising:
passing the feed stream to the simulated moving bed adsorption zone with a valve having a domed head; and,
recovering the extract stream from the simulated moving bed adsorption zone through the valve.

5. The method of claim 4 further comprising:
flushing the domed head of the valve with a portion of the second bottoms stream from the second fractionation zone to provide a flush fluid.

6. The method of claim 5 further comprising:
recovering the flush fluid as a recovered flush fluid from at least one of the rounded top head of the at least one vessel, the rounded bottom head of the at least one vessel, or the domed head of the valve; and,
recycling the recovered flush fluid back to at least one of the rounded top head of the at least one vessel, the rounded bottom head of the at least one vessel, or the domed head of the valve.

7. The method of claim 1 further comprising:
flushing the rounded top head of the at least one vessel and the rounded bottom head of the at least one vessel with a second flush fluid.

8. The method of claim 7, wherein the second flush fluid is utilized during a startup of the simulated moving bed adsorption zone.

9. The method of claim 7, wherein the second flush fluid is utilized if a contamination has been detected.

10. The method of claim 1 wherein the simulated moving bed adsorption zone includes a second vessel having a rounded top head and a rounded bottom head and further comprising:
flushing the rounded top head of the second vessel with a portion of the second bottom stream from the second fractionation zone; and,
flushing the rounded bottom head of the second vessel with a portion of the second bottom stream from the second fractionation zone.

11. A method for the recovery of paraxylene from a feed stream comprising:
passing a feed stream through a valve in an adsorption zone having at least one vessel in which paraxylene is adsorbed, the at least one vessel having a rounded top head and a rounded bottom head;
withdrawing a raffinate from the adsorption zone through a valve;
passing a desorbent into the at least one vessel to desorb the paraxylene in an extract stream;
withdrawing the extract stream from the adsorption zone through a valve;
passing the extract stream from a valve to a first fractionation zone in which the extract stream is separated into an overhead stream comprising a desorbent rich stream and a bottoms stream comprising paraxylene and heavy compounds;
passing the bottoms stream of the first fractionation zone to a second fractionation zone in which the bottoms stream of the first fractionation zone is separated into a second overhead stream comprising a paraxylene rich stream and a second bottoms stream comprising the heavy compounds;
recovering a portion of the second bottoms stream as a flush fluid;
flushing the top head of the at least one vessel with the flush fluid;
flushing the bottom head of the at least one vessel with the flush fluid; and,
flushing a valve with the flush fluid.

12. The method of claim 11 further comprising:
recovering the flush fluid used to flush the bottom head of the at least one vessel; and,
passing the flush fluid used to flush the bottom head of the at least one vessel to a third fractionation zone.

13. The method of claim 12 further comprising:
recovering the flush fluid used to flush the valve; and,
recycling the flush fluid used to flush the valve as a recycled flush fluid.

14. The method of claim 13 further comprising:
recovering the flush fluid used to flush the top head of the at least one vessel; and,
recycling the flush fluid used to flush the top head of the at least one vessel as a recycled flush fluid.

15. The method of claim 11 further comprising:
flushing the valve, the top of the first chamber, and the bottom of the first chamber with the desorbent until a flow level of the bottom stream from the second separation zone reaches a predetermined level.

16. The method of claim 15 wherein the desorbent is toluene.

17. The method of claim 14 further comprising:
flushing the valve, the top of the first chamber, and the bottom of the first chamber with the desorbent if a contamination of the recycled flush fluid is detected.

* * * * *